United States Patent [19]

Colombo et al.

[11] 4,329,052
[45] May 11, 1982

[54] METHOD AND APPARATUS FOR THE MEASUREMENT OF CELL SIZE IN A FOAM STRUCTURE

[75] Inventors: Edward A. Colombo, Fairport; James T. Tsai, Victor, both of N.Y.

[73] Assignee: Mobil Oil Corporation, New York, N.Y.

[21] Appl. No.: 24,770

[22] Filed: Mar. 28, 1979

Related U.S. Application Data

[63] Continuation of Ser. No. 820,993, Aug. 1, 1977, abandoned, which is a continuation of Ser. No. 641,130, Dec. 15, 1975, abandoned.

[51] Int. Cl.³ .............................................. G01N 15/07
[52] U.S. Cl. .................................... 356/335; 356/239
[58] Field of Search ....................... 356/335, 442, 239

[56] References Cited

U.S. PATENT DOCUMENTS

| | | | |
|---|---|---|---|
| 3,572,947 | 3/1971 | Sepall | 356/239 X |
| 3,574,470 | 4/1971 | Paine | 250/571 X |
| 3,786,261 | 1/1974 | Tucker | 356/442 X |
| 3,879,129 | 4/1975 | Inoue | 356/442 X |

Primary Examiner—John K. Corbin
Assistant Examiner—Matthew W. Koren
Attorney, Agent, or Firm—C. A. Huggett; M. G. Gilman; J. P. O'Sullivan, Sr.

[57] ABSTRACT

A method and apparatus are provided to continuously monitor and measure the average size of individual foam cells contained in a foam structure, such as polystyrene foam for example, as it is being fabricated. Such an arrangement permits the prompt adjustment of process conditions and/or the concentration of nucleating agents in the extrusion system in the event the size of the individual cells in the foam structure varies from a preselected standard.

2 Claims, 3 Drawing Figures

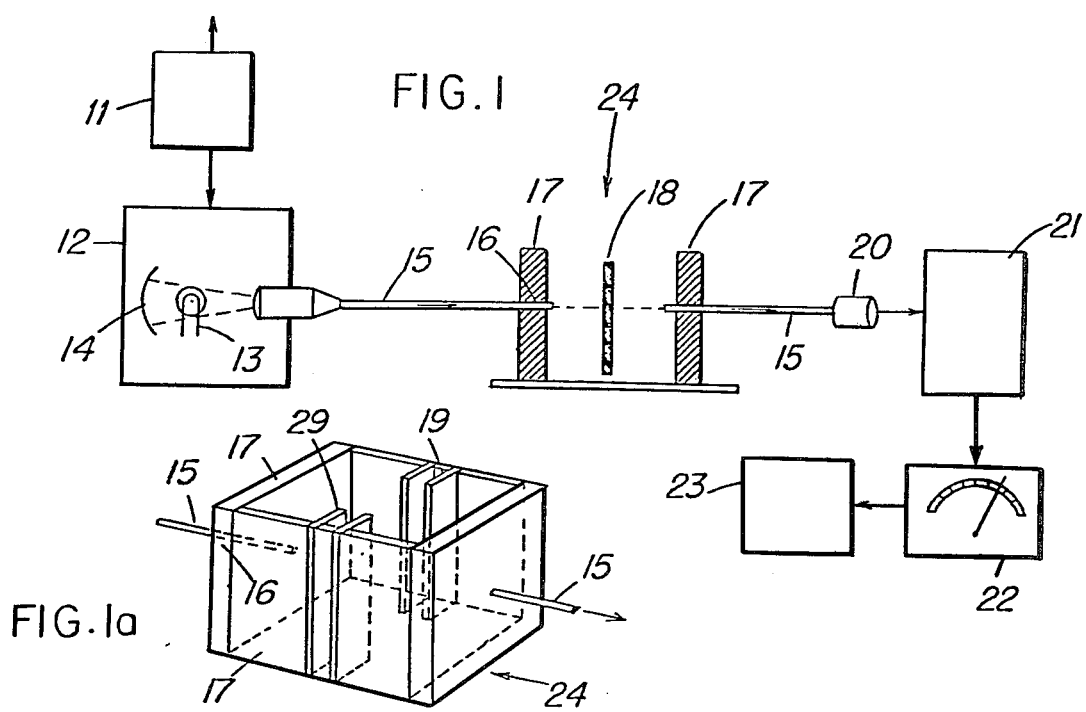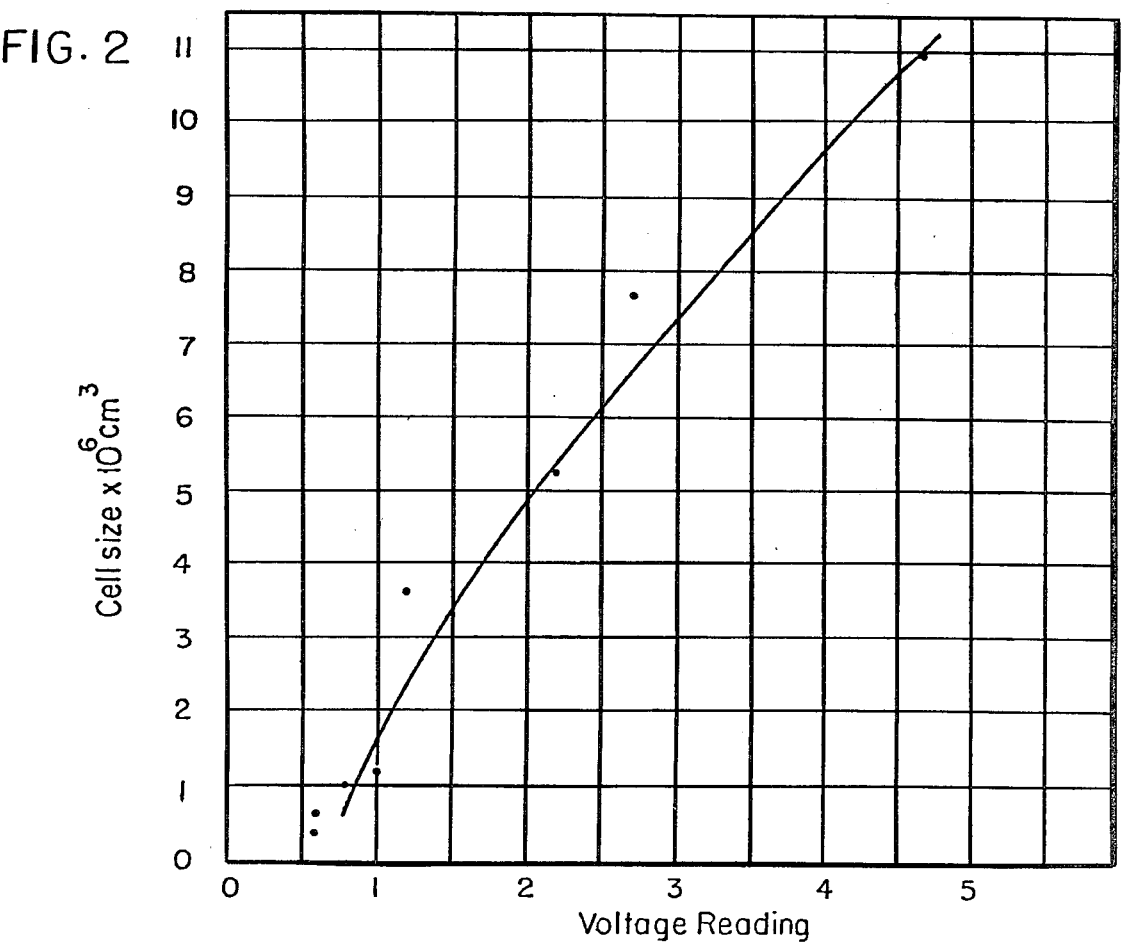

METHOD AND APPARATUS FOR THE MEASUREMENT OF CELL SIZE IN A FOAM STRUCTURE

This is a continuation of Ser. No. 820,993, filed Aug. 1, 1977, now abandoned which is a continuation of Ser. No. 641,130, filed Dec. 15, 1975, now abandoned.

BACKGROUND OF THE INVENTION

1. Field of the Invention

The present invention relates to a method and apparatus which employ transmitted light to continuously measure the individual cell size of cells contained in an extruded plastic foam product such as polystyrene foam. By continuously monitoring this foam characteristic, i.e. cell size, the variation of which has a pronounced effect upon the physical properties of the foam, prompt processing and/or material feed (e.g., blowing agent, nucleating agent, etc.) adjustments may be made to bring the cell size back into a specified range in the event that it deviates therefrom.

2. Description of the Prior Art

It is known in the prior art that during the extrusion of polymer foam, cell size is the structural parameter which can be modified most readily and, furthermore, has a pronounced effect on the foam's properties. These properties include compressive strength, tensile strength, elongation at break, tear strength and thermal insulating values. Cell size can be varied by orders of magnitude in a full scale production process by manipulating the necessary process parameters, nucleating agent, melt temperature, and so forth. The quantification of cell size is, under normal circumstances, tedious and time consuming. Normally a thin section of foam is prepared using a suitable cutting device, microtome or its equivalent. The sample is then examined under a microscope or other suitable device and an attempt is made to characterize the cell size by measuring the mean diameter of the cell or counting the number of cells contained in a given area. Obviously, these prior art methods do not lend themselves to continuous monitoring nor do they necessarily reflect the average cell size of the sample under investigation, since distribution of cell sizes occurs in most foam polymer systems and single point measurements cannot always be translated into an average measurement. In addition, these kinds of cell size quantification can be costly in a production situation. Poor quality and/or "off-specification" material can be manufactured for long periods of time while an out-of-line cell size measurement is being made. Accordingly, it is an object of the present invention to provide a continuous in-line method and apparatus for determining the cell size of polymeric foams as they are extruded. Further, the present invention provides an arrangement whereby in the event the monitored cell size of the foam is not within product specifications, automatic adjustments may be made to extrusion line conditions and/or to the extrusion feed materials to bring the cell size of the foam material within the desired specifications.

SUMMARY OF THE INVENTION

The present invention relates to an apparatus and method for determining the average individual cell size of a plastic foam structure which comprises directing a beam of light onto one surface of the foam, receiving and collecting the light which is transmitted through said foam with a detector photocell, electrically measuring the amount of light energy received by said photocell whereby said light energy measurement is directly converted to said cell size. In accordance with the method of the present invention, it has been found that as the individual cell size in a foam structure decreases, the percentage of light which is transmitted through a structure with such decreasing cell size is reduced. In other words, as the cell size decreases, the percentage of light transmitted through a foam specimen also decreases. Accordingly, by measuring the percent of light transmitted through a series of foam samples with varying cell size, the percent of light transmitted which is measured is in direct relationship with the size of the individual cells in the foam.

BRIEF DESCRIPTION OF THE DRAWINGS

FIG. 1 is a schematic diagram of an apparatus which may be employed in the practice of the present invention.

FIG. 1(a) is a schematic representation of a foam sample holder employed in the present apparatus.

FIG. 2 is a master-curve chart showing cell size as a function of a voltmeter readout.

DESCRIPTION OF SPECIFIC EMBODIMENTS

In general, radiant energy striking matter may be absorbed, transmitted or reflected. The fraction of the total energy absorbed is called absorbtivity, the fraction transmitted is the transmissivity, and the fraction reflected is the reflectivity or, expressed otherwise:

$$absorbtivity + transmissivity + reflectivity = 1$$

A body having an absorbtivity of unity is called a black body. If absorbtivity plus reflectivity are equal to one for a substance, it is said to be opaque. The comparative opacity of a disperse system, such as a solid thermoplastic foam, is due to the scattering of incident light by multiple reflection and refraction caused by the cell walls of the individual cells which constitute the foam structure. In accordance with the present invention, the loss of light energy on transmission through a piece of foam has been found to be a function of the cell size. This loss of light energy is expressed hereinafter in terms of percent transmission, which is defined as the ratio of the incident light to the emergent light.

Techniques for the extrusion of polystyrene foam are well known in the art and a particularly desirable method is disclosed in U.S. Pat. No. 3,482,006, the disclosure of which is incorporated herein by reference. Generally, prior to extrusion, polystyrene pellets are coated with or admixed with a nucleating agent. Typical of such nucleating agents is a mixture of sodium bicarbonate and citric acid although others may be employed. The nucleating agent which is admixed with the polystyrene serves to control the cell size of the cells contained in the extruded foam product. Following admixing of the nucleating agent with the polystyrene resin, the mixture is fed to a standard rotating screw type extruder, wherein it is thoroughly mixed and melted as it is advanced towards the exit end of the extruder. A blowing agent such as pentane or isopentane is injected into the extruder downstream of the feed hopper. The pentane blowing agent is thoroughly admixed with the melted polystyrene and nucleating agent and this mixture is eventually extruded from the extrusion system through a die, either in the form of a flat foam sheet or a tubular structure which is subsequently cooled, and the polystyrene foam sheeting recovered. As hereinbefore discussed, it is of prime importance that the size of the individual cells of the foam structure be regulated within close tolerances. Cell size variation in a finished foam product has a pronounced effect on the properties of the foam structure. Although foam cell size may be controlled or rather varied by varying process parameters, the prime control means for adjusting foam cell size is usually by control of the concentration of nucleating agents in the extrusion system. This concentration however, during continuous extrusion processes, may vary somewhat due to the vagaries of the system such as erratic feed at the nucleant feed hopper, incomplete or non-uniform mixture of the nucleants with the resin, and other undesirable conditions. Applicants have now found that irregularities in the size of the cell in the extruded foam sheet may be continuously monitored and quickly discovered and corrected by continuous measurement of the percent of light transmitted through the foam sheet.

One form of apparatus which may be employed to practice the method of the present invention is schematically represented in FIG. 1 and FIG. 1(a). As shown in FIG. 1, incident light is provided by light source 13 which is powered from a voltage source (not shown). The incident light is provided by a 120 volt 500 watt bulb 13 in a parabolic reflector 14. Current is supplied to bulb 13 by an accumulator cell through a constant voltage transformer 11. The foam sample holding cell, generally designated as 24, as particularly shown in FIG. 1(a) comprises sample enclosure walls 17, two opposite walls of which are provided with guide tracks 19 for supporting and positioning a foam sheet sample. Incident light from source 13 is transmitted through fibre-optic wire material 15 to provide a flexible, consistent light path. The fibre-optics wire is a randomly arranged high-transmission glass fibres sheathed in plastic tubing with epoxy potted, ground and polished ends. In the following example, the fibre optics wire employed has a numerical aperture of 0.55 and takes a cone of light 60° with a fibre bundle diameter of $\frac{3}{8}$ inches. Material 15 carries the incident light through hole 16, $\frac{3}{8}$ inches in diameter, which is centered in one of the walls 17. The incident light subsequently passes to the surface of foam sample 18 and light transmitted therethrough is picked up by fibre-optic material 15 positioned in and passing through the opposite wall surface as shown in FIG. 1. The transmitted light is carried by fibre-optic 15 to photocell 20. Photocell 20 is of the selenium rectifying type and is connected to a low resistance microammeter 21. The selenium cell is circular with an area of one square centimeter.

Standardization of light source 13 is achieved by continual reference to an opal glass screen placed in the position of the foam sample cell where the light intensity was adjusted to give a value equivalent to a full-scale deflection with the empty foam cell in position. The microammeter reading is transformed to a 5 volt voltage meter 22 by which the intensity of transmitted light can be registered on a strip chart recorder 23.

In the following Table I data is presented for a series of examples wherein the reading on the aforedescribed voltage meter is correlated with the individual cell size in a series of polystyrene foam samples. It will be noted how the cell size varies dependent on the concentration of nucleating agents employed, an increase of the nucleating agents concentration in the extrusion system resulting in the production of foam having a smaller individual cell size and vice-versa. The nucleating system employed to produce the individual foam samples in the following examples of Table I was a mixture of anhydrous citric acid and sodium bicarbonate, the bicarbonate being present in a weight ratio to the acid of about 1:0.76. The polystyrene resin employed was identified by the manufacturer as Dow-685 general purpose polystyrene. The extrusion apparatus employed to produce the foam sample is described in U.S. Pat. No. 3,482,006.

EXAMPLE 1

Polystyrene resin pellets were admixed with a nucleating agent mixture comprising sodium bicarbonate and anhydrous citric acid. The nucleating agents constituted 0.58% by weight based upon the total weight of the polystyrene feed charge. The acid to bicarbonate ratio was 1:0.76. These materials were continuously fed into the feed hopper of a 2½ inch diameter screw extruder having a L/D ratio of 24:1. The extruder was operated at an extrusion rate of 150 lb./hr. and the extrusion screw was internally cooled with water at a temperature of about 72° F. By means of extruder barrel heaters, the portion of the extruder barrel surrounding the feed zone of the extruder was maintained at a temperature of about 220° F. In the melting zone, pentane injection zone, and the mixing zone, the extruder barrel was maintained at a temperature of from about 400° F. to 450° F. A liquid pentane blowing agent was injected through the extruder barrel, about 5% by weight of pentane based upon the total weight of resin and nucleating agent, and into the polystyrene composition at a point beyond the feed section where the polystyrene was in a molten condition. The molten mass was than passed through the extruder mixing zone and finally through the cooling section of the extrusion system before being extruded through an annular die orifice, affixed to the terminal end of the extruder.

Samples of the foam produced in accordance with the foregoing example were then measured for light transmittance, expressed in terms of voltage, with the apparatus hereinabove described and as represented in FIG. 1. The size of the individual foam cells in the foam sample were then physically measured under magnification (100 x).

The procedure of Example I was employed to produce additional samples in Examples 1 through 9 inclusive, the concentration of nucleating agents being varied, as shown in the following Table I.

TABLE I

| | CORRELATION OF VOLTAGE METER READING WITH AVERAGE CELL RADIUS | | | | |
|---|---|---|---|---|---|
| Example | Gauge (in.) | Density gm/cc | Cell Radius Measured (Mills) | Nucleating Agents (%) | Voltage Reading |
| 1 | 0.048 | 0.141 | 5.43 | 0.15 | 4.70 |
| 2 | 0.061 | 0.109 | 4.80 | .24 | 2.75 |
| 3 | .076 | 0.084 | 4.25 | .33 | 2.20 |
| 4 | .082 | 0.078 | 3.76 | .42 | 1.40 |
| 5 | .093 | 0.071 | 2.95 | .49 | 1.05 |
| 6 | .095 | 0.067 | 2.62 | .57 | 1.00 |
| 7 | .097 | 0.067 | 2.43 | .65 | 0.80 |
| 8 | .100 | 0.066 | 2.10 | .74 | 0.60 |
| 9 | .101 | 0.066 | 1.70 | .82 | 0.50 |

As shown in FIG. 2, the data obtained from the preceding examples was plotted to obtain a master curve correlating the voltage readout from the voltmeter of the apparatus as shown in FIG. 1 with the cell radius of individual cells in the foam samples. In will be noted that, in accordance with the data, as the amount of nucleating was varied, the size of the cells changed, i.e. increasing the nucleating agent concentration resulted in a decrease in the foam cell radius and vice-versa. By employing the master curve of FIG. 2, it is now possible to obtain the cell size of a given foam sample utilizing the light transmission device as shown in FIG. 1. and translating the voltage readout directly to the foam size of the cells in the sample being measured. Obviously, this may be done either out of line or, preferably, in-line. For example, the heads of fibre-glass tubes 15 which transfer the incident light and transmitted light were positioned 2 inches above and beneath a continuously advancing foam sheet on a production line. The optic-fibre tubes were otherwise connected as shown in FIG. 1. With this arrangement, the variation of the cell size on the production extrusion line was automatically determined and continuously recorded utilizing a strip chart recorder. Moreover, whenever it appeared that the cell size was either too large or too small with respect to the particular cell size desired, a simple adjustment was made, (automatically, e.g. by computer control) to either increase or decrease the concentration of the nucleating agent being admixed with the resin prior to introduction of the mixture into the extruder system. As hereinbefore noted, it is also possible to vary other process parameters to obtain variation in cell size such as, for example, density blowing agent concentration, melt temperature and others.

Although the present invention has been described with preferred embodiments, it is to be understood that modifications and variations may be resorted to without departing from the spirit and scope of this invention, as those skilled in the art will readily understand. Such variations and modifications are considered to be within the purview and scope of the appended claims.

What is claimed is:

1. A continuous method for controlling the average individual cell size of a moving plastic foam structure continuously emerging from a production extrusion source which comprises: illuminating a portion of the surface of said foam structure;

receiving and collecting the light which is transssmitted through said foam with a detector photocell;

continuously electrically measuring the amount of light energy received by said photocell whereby said light energy measurement is correlated to average cell size;

and controlling production process parameters to obtain a foam structure of predetermined average cell size in response to a predetermined amount of light energy received by said photocell.

2. An apparatus for continuously controlling the average individual cell size of a moving plastic foam structure emerging from a production extrusion source which comprises:

a light source;

means for moving said foam structure past said light source;

means for receiving and transmitting light which is transmitted through said foam structure to a photocell device;

means for measuring the electrical energy output of said photocell device for direct correlation to average cell size;

and means responding to said electrical energy output to control production process parameters to obtain a foam structure of predetermined average cell size.

* * * * *